US011999674B2

(12) United States Patent
Klinkenberg et al.

(10) Patent No.: US 11,999,674 B2
(45) Date of Patent: Jun. 4, 2024

(54) BUTADIENE TELOMERIZATION CATALYST PREPARATION AND USE THEREOF

(71) Applicant: Dow Global Technologies LLC, Midland, MI (US)

(72) Inventors: Jessica L. Klinkenberg, Midland, MI (US); John R. Briggs, Midland, MI (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 18/332,907

(22) Filed: Jun. 12, 2023

(65) Prior Publication Data

US 2023/0331643 A1     Oct. 19, 2023

Related U.S. Application Data

(62) Division of application No. 17/703,458, filed on Mar. 24, 2022, now Pat. No. 11,713,286, which is a division of application No. 15/564,543, filed as application No. PCT/US2016/025472 on Apr. 1, 2016, now Pat. No. 11,312,670.

(60) Provisional application No. 62/145,650, filed on Apr. 10, 2015.

(51) Int. Cl.
| | |
|---|---|
| *C07C 11/02* | (2006.01) |
| *B01J 31/24* | (2006.01) |
| *C07C 2/40* | (2006.01) |
| *C07C 41/06* | (2006.01) |

(52) U.S. Cl.
CPC .......... *C07C 2/406* (2013.01); *B01J 31/2438* (2013.01); *C07C 41/06* (2013.01); *B01J 2231/20* (2013.01); *B01J 2531/824* (2013.01); *C07C 2531/24* (2013.01)

(58) Field of Classification Search
None
See application file for complete search history.

(56) References Cited

U.S. PATENT DOCUMENTS

| | | | |
|---|---|---|---|
| 3,026,327 | A | 3/1962 | Epstein et al. |
| 8,558,030 | B2 | 10/2013 | Briggs et al. |
| 8,779,164 | B2 | 7/2014 | Leeuwen et al. |
| 8,921,346 | B2 | 12/2014 | Leeuwen et al. |
| 2016/0271601 | A1 | 9/2016 | Launay et al. |

FOREIGN PATENT DOCUMENTS

| | | |
|---|---|---|
| EP | 0450707 A1 | 10/1991 |
| EP | 0561779 A1 | 9/1993 |
| WO | 2012087686 A1 | 6/2012 |
| WO | 2015088867 A2 | 6/2015 |

OTHER PUBLICATIONS

Behr et al. "Octadienyl-Bridged Bimetallic Complexes of Palladium as Intermediates in Telomerization Reactions of Butadiene", Organometallics, 1986, 5, 514-518.
Benn et al., "Intermediates in the Palladium-Catalyzed Reactions of 1, 3-Dienes 2 Preparation and Structure of (n1,n3-Octadiendiyl)palladium Complexes", Organometallics, 1985, 4, 1945-1953.
Brenstrum et al., "Phosphaadamantanes as Ligands for Palladium Catalyzed Cross-Coupling Chemistry: Library Synthesis, Characterization, and Screening in the Suzuki Coupling of Alkyl Halides and Tosylates Containing 6-Hydrogens with Boronic Acids and Alkylboranes", J. Org. Chem., 2004, 69, 7635-7639.
Epstein et al., "A Novel Phosphorous Heterocyclic System for the Reactions of Phosphine and Primary Phosphines with 2,4-Pentanedione", J. Am. Chem. Soc., 1967, 83, 3279-3282.
Hausoul et al., "Facile Access to Key Reactive Intermediates in the Pd/PR3-Calalyzed Telomerization of 1,3-Butadiene", Angew. Chem. Int. Ed., 2010, 49, 7971-7975.
Hausoul et al., "Mechanistic Study of the Pd/TOMPP-Catalyzed Telomerization of 1,3-Butadiene with Biomass-Based Alcohols: On the Reversibility of Phosphine Alkylation", ChemCatChem, 2011, 3, 845-852.
Hausoul et al., "Mechanistic Study of the Pd/TOMPP-Catalyzed Telomerization of 1,3-Butadiene: Influence of Aromatic Solvents on Bis-Phosphine Complex Formation and Regio Selectivity", Organometallics, 2013, 32, 5047-5057.
International Preliminary Report on Patentability pertaining to PCT/US2015/068483, dated Jun. 2016.
International Preliminary Report on Patentability pertaining to PCT/US2016/025472 dated Oct. 10, 2017.
International Search Report and Written Opinion pertaining to PCT/US2014/068483, dated Sep. 2015.
International Search Report and Written Opinion pertaining to PCT/US2016/025472 dated Jul. 11, 2016.
Jackstell et al., "An Industrially Viable Catalyst System for Palladium-Catalyzed Telomerizations of 1,3-Butadiene with Alcohols", Chem. Eur. J., 2004, 10, 3891-3900.
Protopopov et al., "Reactions of Phenol Ethers with Phosphorous Trichloride 11: Reaction of m-Dimethozybenzene with Phosphorus Trichloride", Zhurnal Obshchei Khimii, 1964, 34, 1446-1449.
Storzer et al., "(Cyclohexylmethylphenylphosphine)[1-e1:6-8-e3)-octa-2,6-diene-1,8-diyl]palladium(II) as a Model for Key Intermediates in Enantioselective Reactions of 1,3-Butadiene Catalyzed by Palladium (0)", Organometallics, 2005, 24, 514-520.

(Continued)

*Primary Examiner* — Yun Qian
(74) *Attorney, Agent, or Firm* — Dinsmore & Shohl LLP

(57) ABSTRACT

Catalyst compositions are prepared by contacting a palladium source and 1,3,5,7-tetramethyl-6-(2,4-dimethoxyphenyl)-2,4,8-trioxa-6-phosphaadamantane and a methoxyoctadiene compound, in a primary aliphatic alcohol, under suitable conditions including a ratio of equivalents of palladium to equivalents of 1,3,5,7-tetramethyl-6-(2,4-dimethoxyphenyl)-2,4,8-trioxa-6-phosphaadamantane ranging from greater than 1:1 to 1:1.3. The result is a complex of palladium, a 1,3,5,7-tetramethyl-6-(2,4-dimethoxyphenyl)-2,4,8-trioxa-6-phosphaada-mantane ligand, and a ligand selected from a methoxyoctadiene ligand, an octadienyl ligand, or a protonated octadienyl. Such complexes may, in solution, exhibit surprising solubility and storage stability and are useful in the telomerization of butadiene, which is a step in the production of 1-octene.

4 Claims, No Drawings

(56) References Cited

OTHER PUBLICATIONS

Vollmuller et al., "Palladium-Catalyzed Reactions for the Synthesis of Fine Chemicals, 14, Control of Chemo- and Regioselectivity in the Palladium-Catalyzed Telomerization of Butadiene with Methanol", Catalysis and Mechanism, 2000, 8, 1825-1832.
Vollmuller et al., "Palladium-Catalyzed Reactions for the Synthesis of Fine Chemicals, 16, Highly Efficient Palladium-Catalyzed Telomerization of Butadiene with Methanol", Adv. Synth. Catal., 2001, 343, 1, 29-33.
Office Action dated Apr. 11, 2019 pertaining to U.S. Appl. No. 15/030,625, filed Apr. 20, 2016, 20 pgs.
Notice of Allowance and Fee(s) Due dated Oct. 18, 2019 pertaining to U.S. Appl. No. 15/030,625, filed Apr. 20, 2016, 13 pages.
Office Action pertaining to U.S. Appl. No. 15/030,625 dated Jul. 10, 2018.
Examination Report pertaining to European Patent Application No. 14827296.6, dated May 15, 2019.
Office Action pertaining to corresponding Chinese Patent Application No. 201680020659.0, dated Jun. 17, 2019.
Adjabeng, G. et al., "Novel Class of Tertiary Phosphine Ligands Based on a Phospha-adamantane Framework and Use in the Suzuki Cross-Coupling Reactions of Aryl Halides under Mild Conditions," Organic Letters, vol. 5, No. 6, pp. 953-955 (2003).
Canadian Office Action pertaining to related Canadian Patent application No. 3,133,814, dated Dec. 2, 2022 5 total pages.
U.S. Office Action pertaining to related U.S. Appl. No. 15/564,543 dated Apr. 18, 2019 11 total pages.
U.S. Office Action pertaining to related U.S. Appl. No. 15/564,543 dated Oct. 9, 2018 20 total pages.
Chinese First Office Action dated Mar. 30, 2018 pertaining to Chinese Patent Ap No. 20140066623.7, dated Mar. 30, 2018 6 total pages.

BUTADIENE TELOMERIZATION CATALYST PREPARATION AND USE THEREOF

This application is a divisional application of U.S. Nonprovisional application Ser. No. 17/703,458 filed on Mar. 24, 2022, entitled "Butadiene Telomerization Catalyst Preparation and Use Thereof," which is a divisional application of U.S. Non-Provisional application Ser. No. 15/564,543, filed on Oct. 5, 2017, entitled "Butadiene Telomerization Catalyst and Preparation Thereof," which is a national stage entry of PCT Application PCT/US2016/025472, which claims priority to U.S. Provisional Application No. 62/145,650 entitled "Butadiene Telomerization Catalyst and Preparation Thereof," each of which are incorporated herein by reference in their entireties.

This invention relates generally to preparation of a butadiene telomerization catalyst precursor.

Because octane has important and commercially valuable uses in the gasoline fuel industry, improved processes to produce its convenient starting material, 1-octene, have long been sought. One of the steps in producing 1-octene is the telomerization of butadiene. Examples of processes to telomerize butadiene include that disclosed in U.S. Pat. No. 8,558,030, which is a process that includes contacting butadiene and an organic hydroxyl compound represented by the formula ROH, where R is a substituted or unsubstituted $C_1$-$C_{20}$ hydrocarbyl and the organic hydroxyl compound is not glycerol, in a reaction fluid in the presence of a palladium catalyst and a phosphine ligand represented by formula $PAr_3$, wherein each Ar is independently a substituted or unsubstituted aryl having a hydrogen atom on at least one ortho position, and at least two Ar groups are ortho-hydrocarboxyl substituted aryls. The phosphine ligand has a total of 2, 3, 4, 5 or 6 substituted or unsubstituted $C_1$-$C_{20}$ hydrocarboxyls and, optionally, two adjacent substituents on an Ar group can be bonded to form a 5- to 7-membered ring.

A typical process for preparing a catalyst precursor used in telomerization of butadiene to produce 1-octene involves batchwise dissolution of one equivalent of palladium acetyl acetonate ([Pd(acac)$_2$]) and two equivalents of a triarylphosphine ($PAr_3$) (e.g., triphenyl phosphine (TPP) or tris(5-chloro-2-methoxyphenyl)phosphine (TCMPP) in methanol. This precursor is stabilized by acetic acid that is also added during pre-catalyst solution make-up, resulting in a salt that is soluble in methanol and in a +2 oxidation state. Under telomerization reaction conditions, the palladium (Pd)(II)-containing catalyst precursor appears to be reduced by a sodium methoxide promoter in methanol in the presence of 1,3-butadiene to a palladium(Pd(0)) bis-phosphine complex designated as [Pd(PPh$_3$)$_2$]. Subsequent addition of 1,3-butadiene results in formation of a (PPh$_3$)$_{1\ or\ 2}$-Pd-(octadienyl) complex. Further reaction with methanol leads to formation of either 1-methoxy-2,7-octadiene (MOD-1) or 3-methoxy-1,7-octadiene (MOD-3). At low temperatures such as those within a range of from 25 degrees Celsius (° C.) to 60° C., the reaction may include an induction period due to reduction of the Pd(II) species to an active Pd(0) complex. This reduction may occur more slowly than the telomerization reaction, and therefore the induction period may occur before the telomerization reaction can attain its maximum rate. Those skilled in the art therefore may desire to reduce, preferably substantially reduce, and more preferably eliminate, this induction period.

Hausoul, et al., in "Facile Access to Key Reactive Intermediates in the Pd/PR$_3$-Calalyzed Telomerization of 1,3-Butadiene," *Angew. Chem. Int. Ed.* 2010, 49, 7971-7975, notes that Pd-catalyzed telomerization of 1,3-dienes is an important atom-efficient transformation that provides an economically attractive route to production of $C_8$ bulk chemicals such as 1-octanol and 1-octene. Hausoul reports on preparation of catalyst complexes that include phosphine ligands such as PPh$_3$ (triphenylphosphine), TOMPP (tris(2-methoxyphenyl)phosphine) and TPPTS (3,3',3"-phosphinidynetris(benzenesulfonic acid) trisodium salt). The preparation uses a solvent mixture such as a 1:1 volume mixture of dichloromethane and methanol.

Benn, et al., in "Intermediates in the Palladium-Catalyzed Reactions of 1,3-Dienes. 2. Preparation and Structure of ($\eta^1$,$\eta^3$-Octadiendiyl)palladium Complexes," Organometallics 1985, 4, 1945-1953, reports preparation of a series of ($\eta^1$,$\eta^3$-octadiendiyl) palladium complexes, [Pd(L)($\eta^1$,$\eta^3$—$C_8H_{12}$)] and [Pd(L) $\eta^1$,$\eta^3$-Me$_2$C$_8$H$_{10}$)], by reacting bis($\eta^3$-2-methylallyl) palladium with donor ligands and butadiene or isoprene, and tetrahydrofuran (THF) as a solvent.

Behr, et al., in "Octadienyl-Bridged Bimetallic Complexes of Palladium as Intermediates in Telomerization Reactions of Butadiene," Organometallics 1986, 5, 514-518, discusses preparation of the title compounds using a solvent such as methanol, THF or benzene.

Hausoul, et al., in "Mechanistic Study of the Pd/TOMPP-Catalyzed Telomerization of 1,3-Butadiene with Biomass-Based Alcohols: On the Reversibility of Phosphine Alkylation," ChemCatChem 2011, 3, 845-852, discloses testing of several catalyst systems, with emphasis upon Pd/TOM PP (tris(2-methoxyphenyl)phosphine).

Vollmüller, et al., in "Palladium-Catalyzed Reactions for the Synthesis of Fine Chemicals, 16, Highly Efficient Palladium-Catalyzed Telomerization of Butadiene with Methanol," *Adv. Synth. Catal.* 2001, 343, 1, 29-33, details use of methanol under argon to prepare a catalyst precursor from triphenylphosphine and palladium(II) acetate.

Jackstell, et al., in "An Industrially Viable Catalyst System for Palladium-Catalyzed Telomerizations of 1,3-Butadiene with Alcohols," *Chem. Eur. J.* 2004, 10, 3891-3900, describes use of methanol in preparation of catalyst precursors.

Vollmüller, et al., in "Palladium-Catalyzed Reactions for the Synthesis of Fine Chemicals, 14, Control of Chemo- and Regioselectivity in the Palladium-Catalyzed Telomerization of Butadiene with Methanol," Catalysis and Mechanism 2000, 8, 1825-1832, uses mono(phosphane)-palladium(0)-diallyl ether complexes, Ar$_3$P-Pd(CH$_2$═CHCH$_2$)$_2$O, as catalysts to dimerize 1,3-diene, specifically butadiene, in the presence of a nucleophile, in this case methanol. MOD-1 is a primary product, but MOD-3 and other materials are present as byproducts. Vollmüller, et al., state that the catalyst does not need to be activated (e.g., by ligand dissociation, reduction, etc.) before entering the catalyst cycle, but does not discuss precatalyst stability.

Hausoul, et al., in "Mechanistic study of the Pd/TOM PP-Catalyzed Telomerization of 1,3-Butadiene: Influence of Aromatic Solvents on Bis-Phosphine Complex Formation and Regio Selectivity," Organometallics, 2013, 32, 5047-5057, reports on Pd/TOM PP-catalyzed telomerization of 1,3-butadiene with phenols such as p-cresol, guaiacol and creosol.

European Patent Specification (EP) 0 561 779 B1 (Bohley, et al.) relates to a process for producing 1-octene. The process comprises: (1) reacting 1,3-butadiene with a primary aliphatic alcohol (e.g., methanol, ethanol, propanol, butanol, ethylene glycol, propylene glycol and glycerol) or aromatic hydroxyl compound having formula R—OH (e.g., phenol, benzylalcohol, cresols, xylenols, naphtol, and polyhydric compounds such as resorcinol, hydroquinone, and pyrocatechol, as well as alkyl-, alkoxy- and/or halogen-substituted aromatic compounds such as methoxyphenol and p-chlorophenol), in the presence of a telomerization catalyst comprising palladium and a tertiary phosphorus ligand compound, to form a 1-substituted-2,7-octadiene of formula CH$_2$=CH—CH$_2$—CH$_2$—CH$_2$—CH=CH—CH$_2$—R in which R represents the residue of the primary aliphatic alcohol or aromatic hydroxy compound; (2) subjecting the 1-substituted-2,7-octadiene to hydrogenation in the presence of a hydrogenation catalyst to form a 1-substituted octane of formula CH$_3$—CH$_2$—CH$_2$—CH$_2$—CH$_2$—CH$_2$—CH$_2$—CH$_2$—R; and (3) decomposing the 1-substituted octane in the presence of a suitable catalyst to form 1-octene. Both palladium(II) compounds and palladium(0) complexes may be used as the catalyst. A catalyst promoter such as an alkali or alkaline earth metal salt appears to be advantageous. Bohley, et al., teach that any solvent that will solubilize 1,3-butadiene, the active hydrogen-containing compound, and the catalyst, ligand and optional promoter components may be used in the process. Suitable inert solvents are a (cyclo)-alkane, an aromatic compound, a polar solvent such as a tertiary alcohol, an amide, a nitrile compound, a ketone, an ester compound, an ether compound, dimethylsulfoxide, sulpholane, and water. While the temperature is not stated to be critical, it ranges from ambient temperature to about 150° C., preferably from about 50° C. to about 100° C., and more preferably from about 70° C. to about 100° C. Pressure is similarly not critical, but is generally between 1 and 40 bars, preferably between 5 and 30 bars, and most preferably between 10 and 20 bars.

U.S. Patent Application Ser. No. 61/915,781, filed Dec. 13, 2013, discloses a process to prepare a telomerization catalyst precursor that comprises dissolving one equivalent of palladium acetyl acetonate and from 1 to 3 equivalents of a tertiary phosphine ligand, under conditions sufficient to form a catalyst precursor. The tertiary phosphine ligand may, in one embodiment, be defined by the formula R1PR$_2$, wherein R1 is an aryl moiety or a substituted aryl moiety or an alkyl moiety or a heteroatom-containing alkyl moiety; P is phosphorus; and R2 is independently a heterocyclic oxaadamantyl group.

In one embodiment the invention provides a catalyst composition useful for catalyzing the telomerization of butadiene comprising a complex comprising palladium, a 1,3,5,7-tetramethyl-6-(2,4-dimethoxyphenyl)-2,4,8-trioxa-6-phosphaadamantane ligand, and a ligand selected from a methoxyoctadiene ligand, an octadienyl ligand, and a protonated octadienyl ligand. In certain particular embodiments the complex is in solution in a primary aliphatic alcohol.

In another embodiment the invention provides a process for preparing a catalyst composition useful for catalyzing the telomerization of butadiene comprising dissolving as reagents a palladium source, 1,3,5,7-tetramethyl-6-(2,4-dimethoxyphenyl)-2,4,8-trioxa-6-phosphaada-mantane, and a methoxyoctadiene compound in a primary aliphatic alcohol, wherein the ratio of equivalents of the palladium to equivalents of the 1,3,5,7-tetramethyl-6-(2,4-dimethoxyphenyl)-2,4,8-trioxa-6-phosphaadamantane ranges from greater than 1:1 to 1:1.3, under conditions sufficient to form a catalyst composition comprising a complex of palladium, a 1,3,5,7-tetramethyl-6-(2,4-dimethoxyphenyl)-2,4,8-trioxa-6-phosphaadamantane ligand, and a ligand selected from a methoxyoctadiene ligand, an octadienyl ligand, and a protonated octadienyl ligand, in the primary aliphatic alcohol.

In yet another embodiment the invention provides a process to telomerize butadiene comprising contacting butadiene and a catalyst composition comprising a complex of palladium, a 1,3,5,7-tetramethyl-6-(2,4-dimethoxyphenyl)-2,4,8-trioxa-6-phosphaadamantane ligand, and a ligand selected from a methoxyoctadiene ligand, an octadienyl ligand, and a protonated octadienyl ligand, under conditions sufficient to telomerize at least a portion of the butadiene.

The present invention provides a catalyst composition; a process to prepare the catalyst composition; and a process using the catalyst composition; all of which relate in general to accomplishing the telomerization of butadiene. Such telomerization is an important first step in the preparation of the commercially valuable chemical 1-octene, which may be, in particular applications, used as an intermediate in the preparation of a wide variety of other chemicals.

The compositions of the present invention may be prepared by a process comprising bringing together, at a minimum, the following components: (1) a source of palladium; (2) from greater than 1 to 1.3 equivalents (based upon 1 equivalent of palladium) of 1,3,5,7-tetramethyl-6-(2,4-dimethoxyphenyl)-2,4,8-trioxa-6-phosphaadamantane; (3) a methoxyoctadiene compound; and (4) a primary aliphatic alcohol. In certain embodiments, what may be termed an optional fifth component, (5) a promoter, and/or what may be termed an optional sixth component, (6) a carboxylic acid (without reference to the actual order of addition and/or whether both optional components are added), may also be included in the process to prepare the inventive catalyst compositions.

Selection of the palladium source is preferably made from Pd(II) compounds and Pd(0) compounds. Pd(II) compounds may include, in non-limiting example, palladium acetylacetonate, palladium formate, palladium acetate, palladium propionate, palladium octanoate, palladium carbonate, palladium hydroxide, palladium citrate, and combinations thereof. Of these, palladium acetylacetonate is particularly preferred, as it offers the advantage of relatively low cost, relatively high reactivity, and convenient commercial availability. Pd(0) compounds that will lead to active palladium species may also be selected, including but not limited to palladium phosphines, palladium alkenes, palladium dienes, palladium nitriles, and combinations thereof. Examples of these may include tetrakis(triphenylphosphine) palladium, bis(1,5-cyclo-octadiene) palladium, bis(dibenzylidene-acetone) palladium, and combinations thereof. Combinations of Pd(II) and Pd(0) compounds may also be selected.

Of particular importance in the present invention is the fact that the process includes contacting a specific tertiary phosphine compound, which is 1,3,5,7-tetramethyl-6-(2,4-dimethoxyphenyl)-2,4,8-trioxa-6-phosphaadamantane, herein denominated as TMPTPA-di-OMe. This oxaphosphaadamantane compound may be schematically represented by the two enantiomeric structures, denominated as structures (I) and (II), hereinbelow:

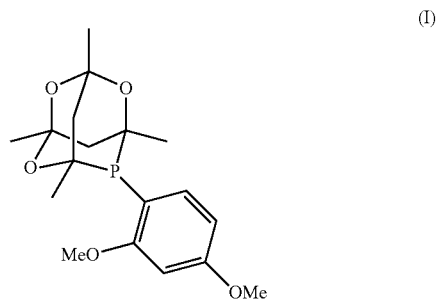

(I)

-continued

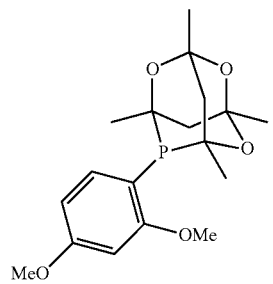

(II)

This ligand may be prepared by, for example, the cross-coupling reaction of the secondary phosphine 1,3,5,7-tetramethyl-2,4,8-trioxa-6-phosphaadamantane with the corresponding 2,4-dimethoxyhalobenzene, which may be accomplished via, e.g., a Suzuki coupling. A Suzuki coupling may be carried out by combining an aryl bromide, such as dimethoxy-bromobenzene, with the secondary phosphine and a base, such as potassium carbonate, in a solvent, such as a mixture of xylenes. This may be stirred under an inert atmosphere and heated to a temperature of about 110° C., for a time period that enables satisfactory completion of the carbon-phosphorus cross-coupling reaction. Following this the product thereof may be diluted and purified by column chromatography, or recrystallized to form a solid. While those skilled in the art will normally be familiar with this reaction, the reader is referred, for greater detail, to, e.g., Brenstrum, et al., "Phosphaadamantanes as Ligands for Palladium Catalyzed Cross-Coupling Chemistry: Library Synthesis, Characterization, and Screening in the Suzuki Coupling of Alkyl Halides and Tosylates Containing 8-Hydrogens with Boronic Acids and Alkylboranes," *J. Org. Chem.* 2004, 69, 7635-7639, which is incorporated herein by reference in its entirety.

In another embodiment, the desired 1,3,5,7-tetramethyl-6-(2,4-dimethoxyphenyl)-2,4,8-trioxa-6-phosphaadamantane compound may be prepared by the reaction of 2,4-dimethoxyphenylphosphine with pentanedione. This approach is illustrated in greater detail in, for example, Epstein and Buckler, "A Novel Phosphorus Heterocyclic System from the Reactions of Phosphine and Primary Phosphines with 2,4-Pentanedione," *J. Am. Chem. Soc.* 1961, 83, 3279-3282, which is incorporated herein by reference in its entirety. In one embodiment of this procedure the pentanedione may be contacted with hydrochloric acid (HCl) in a pressure bottle, and the bottle then successively evacuated, filled with nitrogen, and filled with 2,4-dimethoxyphenylphosphine. Finally, it is shaken under pressure until a precipitate forms, and the precipitate is then diluted, filtered, and dried to recrystallize it. The 2,4-dimethoxyphenylphosphine may be prepared by the reaction of dichloro(2,4-dimethoxy-phenyl)phosphine with lithium aluminum hydride. The dichloro(2,4-dimethoxyphenyl)phosphine may, in turn, be prepared by a ZnCl$_2$-catalyzed Friedel Crafts alkylation of phosphorus trichloride with 1,3-dimethoxybenzene. While those skilled in the art will be very familiar with the aforesaid preparations, the reader is directed, for further detail, to, e.g., Protopopov and Kraft, "Reactions of Phenol Ethers with Phosphorus Trichloride II: Reaction of m-Dimethoxybenzene with Phosphorus Trichloride," *Zhurnal Obshchei Khimii*, 1964, 34, 1446-1449, which is incorporated herein by reference in its entirety.

Those skilled in the art will be able to discern additional methods and means of preparing or otherwise obtaining the 1,3,5,7-tetramethyl-6-(2,4-dimethoxyphenyl)-2,4,8-trioxa-6-phosphaadamantane which is requisite to begin the inventive process as defined herein. It is noted that both of the above generalized methods for its preparation are assumed to produce racemic mixtures, and such racemic mixtures are deemed suitable for use in the present invention without further processing beforehand.

Suitable primary aliphatic alcohols may include, for example, mono- or polyhydric alcohols, which contain primary OH-groups and which can be linear or branched saturated compounds having up to 20 carbon atoms. Such alcohols may also include unsaturated alcohols, such as allyl alcohols. In particular, primary aliphatic alcohols having up to 8 carbon atoms, such as methanol, ethanol, propanol, butanol, ethylene glycol, propylene glycol, glycerol, combinations thereof, and the like, are preferred. More preferably the primary aliphatic alcohol selected is methanol or ethanol, and most preferably it is methanol.

In carrying out the process of the invention, a methoxyoctadiene compound is included as a starting material. This methoxyoctadiene may be preferably selected from 1-methoxy-2,7-octadiene, 3-methoxy-1,7-octadiene, and combinations thereof. Of these, 1-methoxy-2,7-octadiene is more preferred.

As noted hereinabove, in certain embodiments of the invention a promoter, (5), may also be included in preparing the inventive catalyst compositions. The promoter may serve to increase the initial rate of reaction and/or reduce the induction period when the catalyst composition is used in catalyzing the telomerization of butadiene. Such may be selected from, in non-limiting embodiments, alkoxides, enolates, phenoxides, borohydrides, and hydrazides, all of alkali metals; alkaline earth metals and quaternary ammoniums; alkali metal salts; and combinations thereof.

Also as noted hereinabove, another component that may be included in the inventive compositions in certain embodiments is a carboxylic acid, (6). The carboxylic acid may be selected from, for example, aliphatic carboxylic acids having up to about 20 carbon atoms. Such may include, in non-limiting embodiments, formic acid, acetic acid, propionic acid, butyric acid, valeric acid, caproic acid, enanthic acid, caprylic acid, pelargonic acid, capric acid, lauric acid, palmitic acid, stearic acid, benzoic acid, and benzylic acid. Preferred are those carboxylic acids having from 1 to 6 carbon atoms. Aromatic carboxylic acids such as benzoic acid and toluene carboxylic acids, and dibasic acids such as adipic acid and the phthalic acids, may also be selected. Finally, combinations of any of the above may also be employed in the inventive compositions and processes to prepare them.

The proportionality of components requires that, in the inventive catalyst preparation process, the ratio of equivalents of the palladium to equivalents of the specified 1,3,5,7-tetramethyl-6-(2,4-dimethoxyphenyl)-2,4,8-trioxa-6-phosphaadamantane, as added to the primary aliphatic alcohol, range from greater than 1:1 to 1:1.3, and preferably from 1:1.2 to 1:1.3. These limits are defined herein with one significant (i.e., decimal) figure, but it will be understood that additional significant figures may be inferred, particularly with respect to the phrase "greater than 1:1," e.g., this may be read as inclusive of 1:1.11, 1:1.12, 1:1.13, etc. Similarly, the limit "1:1.3" may be read as inclusive of 1:1.31, 1:1.32, 1:1.33, etc. Within these ranges, the process results in a composition exhibiting surprisingly enhanced storage stability and solubility in the primary aliphatic alcohol, which is significantly greater than the same properties as exhibited by certain other oxaphosphaadamantane ligand-containing catalysts. It is noted that, when prepared with starting materials for the complex that are outside of the defined equivalents ratio range (from greater than 1:1 to 1:3), significant storage stability (i.e., more than 3 days) and/or solubility (i.e., producing no substantial amount of precipitate, "substantial" being defined herein as more than 0.5 weight percent (wt %), based upon total solution weight), are surprisingly not obtained. Nonetheless, catalytic effect in the telomerization of butadiene will usually still be experienced where catalyst compositions are prepared based upon ratios of equivalents outside of the greater than 1:1 to 1:1.3 range. It is furthermore noted that, whether preparation includes equivalents within or outside of this range, the complex itself will most often present an approximately 1:1 stoichiometry, of palladium to 1,3,5,7-tetramethyl-6-(2,4-dimethoxy-phenyl)-2,4,8-trioxa-6-phosphaadamantane ligand. It is noted further that complex formation in the present invention is an equilibrium reaction.

It is further preferred that the overall palladium metal concentration range from about 0.02 wt % to about 2 wt %, more preferably from about 0.02 wt % to about 1.5 wt %, still more preferably from about 0.1 wt % to about 1 wt %, and most preferably from about 0.25 wt % to about 0.6 wt %, based on total solution weight. In preferred embodiments the concentration of palladium in the solution may range up to about 20,000 parts per million by weight (ppmw), although a maximum of about 10,000 ppmw is more preferred. The minimum palladium concentration is preferably at least about 500 ppmw, more preferably at least about 2,500 ppmw, and most preferably at least about 3,000 ppmw. It will therefore be noted that the palladium concentration may preferably range from at least about 500 ppmw, more preferably at least about 1,500 ppmx, and most preferably at least about 3,000, to about 20,000 ppmw, more preferably at least about 10,000 ppmw. These preferred levels take into account the fact that, as the composition, most typically in the form of a solution of the catalyst complex, enters the telomerization reactor to take part in a butadiene telomerization, it will be diluted as it is mixed with butadiene and, typically, methanol. The goal, therefore, is to use an amount of palladium in forming the complex that is sufficient to ensure that the palladium concentration in the reactor preferably ranges from about 0.1 ppmw, more preferably from about 3 ppmw, and most preferably from about 5 ppmw, to about 50 ppmw, and more preferably to about 25 ppmw. These levels of palladium help to ensure that the overall catalyst efficiency is acceptable and, in preferred embodiments, within a preferred efficiency range for the commercial scale 1-octene production train in which the catalyst will most desirably be employed.

It is also preferred that the selected methoxyoctadiene compound is added in an amount ranging from about 0.1 wt % (i.e., approximately 1 molar equivalent at 0.1 wt % of palladium) to about 50 wt %, (i.e., approximately 400 molar equivalents at 0.1 wt % palladium). Proportionately higher amounts of the methoxyoctadiene compound may be employed where higher concentrations of palladium, e.g., up to about 2 wt % palladium, are desired. In each case the weight percent is based on total solution weight. The goal is to include in the solution an amount of the methoxyoctadiene compound that is effective such that substantially all, i.e., at least 90 wt %, and more preferably at least 95 wt %, of the palladium therein forms a complex with both the 1,3,5,7-tetramethyl-6-(2,4-dimethoxyphenyl)-2,4,8-trioxa-6-phosphaadamantane ligand and with the ligand derived from the methoxyoctadiene compound. In order to accomplish this, then, the amount of the methoxyoctadiene is preferably included in the preparation process in at least an equivalent molar stoichiometric amount, based upon the amount of palladium. However, a larger amount of the methoxyoctadiene compound will tend to increase the rate at which the inventive catalyst composition forms. Thus, the methoxyoctadiene compound is preferably added in an amount of at least 5 wt %, and more preferably from 5 wt % to 25 wt %, based on total solution weight. Unlike the palladium to 1,3,5,7-tetramethyl-6-(2,4-dimethoxyphenyl)-2,4,8-trioxa-6-phosphaadamantane equivalents ratio, which is important to ensuring that the inventive product can form a storage stable and solubility-enhanced catalyst composition, the operable ranges of the palladium/methoxyoctadiene compound ratio are therefore obviously much broader, though rate effects may of course be very important in the overall design of a 1-octene train.

The optional promoter, (5), where included, is preferably added to the solution in an amount sufficient to achieve a molar ratio of palladium to promoter ranging from 1:0.01, more preferably from 1:0.5, up to 1:1000, preferably up to 1:800, and more preferably up to 1:600. Most preferably the molar ratio of palladium to promoter ranges from 1:2 to 1:10.

The carboxylic acid, (6), where included, is preferably added to the catalyst solution in an amount ranging from 1 to 5 equivalents, based upon 1 equivalent of the palladium. This carboxylic acid compound may, in some embodiments, serve as the source, or one source, of the proton that forms the protonated octadienyl ligand. Such proton may also or alternatively be supplied by the primary aliphatic alcohol. When employed, the identity of the counteranion in solution will be indirectly discernible by those skilled in the art via means such as high resolution mass spectrometry (HRMS), electrospray-ionization mass spectrometry (ESI-MS), and elemental analysis (EA), based upon knowledge of the existence of the catalyst complex.

The aforesaid components are contacted under conditions sufficient to form an amount of a catalyst composition that comprises palladium and, complexed therewith in solution, two ligands. These ligands are the 1,3,5,7-tetramethyl-6-(2,4-dimethoxyphenyl)-2,4,8-trioxa-6-phosphaadamantane ligand, and a ligand derived from the methoxyoctadiene compound. Order of addition of these components is somewhat interchangeable, although it is generally preferred to contact the palladium (i.e., generally the palladium source) and the 1,3,5,7-tetramethyl-6-(2,4-dimethoxyphenyl)-2,4,8-trioxa-6-phosphaadamantane in solution first, followed by the methoxyoctadiene compound. Where a carboxylic acid is included, such is preferably added thereafter, followed by the promoter, where such is to be also included.

Conditions for this contact may include a temperature ranging from about 0° C. to about 100° C., preferably from about 5° C. to about 60° C. Pressure, although not generally considered to be critical, may preferably range from atmospheric (1.0 standard atmosphere, atm, approximately 101.3 kilopascals (kPa)) or slightly lower (e.g., prevailing atmosphere is more typically approximately 0.9 atm, approximately 95.0 kPa) to superatmospheric, e.g., to 10.0 atm, approximately 1,013.3 kPa). A pressure near or at atmospheric is preferred, for reasons of simple convenience. Those skilled in the art will be able to easily determine and optimize conditions of pressure and temperature for the inventive process and therefore for preparation of the inventive catalyst compositions based upon this information.

Reaction times may desirably range from about 1 hour (h) to about 1000 h, preferably from about 2 h to about 100 h, and most preferably from about 24 h to about 72 h. As a general rule, with an increase in either or both the temperature and the methoxyoctadiene compound concentration, formation of the desired palladium complex in solution, containing the desired oxaphosphaadamantane ligand and a ligand obtained from the methoxyoctadiene compound, as discussed hereinbelow, becomes more rapid. Those skilled in the art will recognize that either temperature or methoxyoctadiene compound concentration, or both, may therefore be adjusted to provide a convenient and/or commercially desirable time therefor. For commercial operation, it is desirable to prepare the desired composition in an amount of time ranging from about 2 h to about 100 h. Reaction times of significantly less than about 100 h may be achieved at temperatures ranging from about 30° C. to about 60° C., with concentrations of the methoxyoctadiene compound ranging from about 10 wt % to about 50 wt %, based on total solution weight, i.e., from about 75 molar equivalents to about 400 molar equivalents, based on palladium at 0.1 wt %.

Once the process described hereinabove has been carried out, a complex will have been formed in solution. This complex comprises palladium, a ligand that is 1,3,5,7-tetramethyl-6-(2,4-dimethoxyphenyl)-2,4,8-trioxa-6-phosphaadamantane, and one of three possible ligands derived from the presence of the methoxyoctadiene compound in solution in the primary aliphatic alcohol. The overall complex may be represented using the general formula [(TMPTA-di-OMe)Pd(Y)], wherein TMPTA-di-0 Me is 1,3,5,7-tetramethyl-6-(2,4-dimethoxyphenyl)-2,4,8-trioxa-6-phosphaadamantane; Pd is palladium; and Y may be, as an end product, an octadienyl ligand or a protonated octadienyl ligand, or Y may be, as an intermediate product, a methoxyoctadiene ligand, the exact nature of which will depend upon the starting selected methoxyoctadiene compound. If the starting methoxyoctadiene compound is 1-methoxy-2,7-octadiene, then the ligand derived therefrom will be 1-methoxy-2,7-octadiene, and where the starting methoxyoctadiene compound is 3-methoxy-1,7-octadiene, then the ligand derived therefrom will be 3-methoxy-1,7-octadiene. With time and under the above-described process conditions, both of these intermediate ligands will transform to form either an octadienyl ligand or a protonated octadienyl ligand.

It is also noted that, where Y is a ligand selected from one of the methoxyoctadiene ligands or (non-protonated) octadienyl ligand, the complex is neutral (uncharged). When Y is a protonated octadienyl ligand, the complex is cationic (positively charged). Representative structures for these compositions are shown as (III), (IV), and (V) hereinbelow.

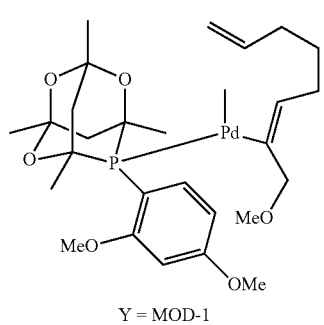

Y = MOD-1

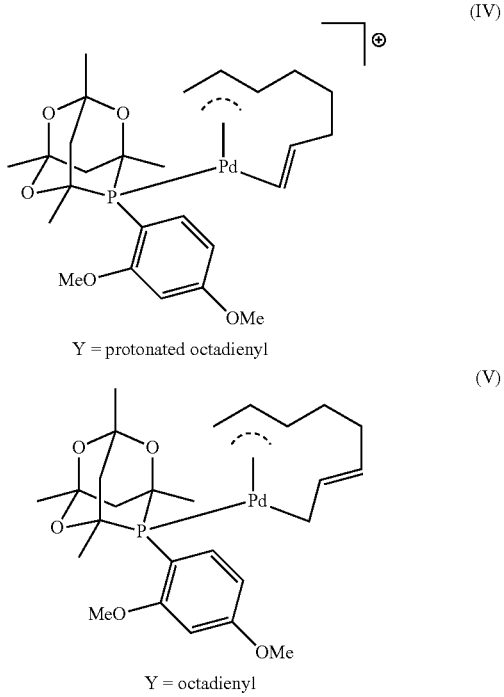

Y = protonated octadienyl

Y = octadienyl

It is therefore to be further understood that, where 1-methoxy-2,7-octadiene is selected as the starting methoxyoctadiene compound, the resulting complex composition will have the formula [(TMPTA-di-OMe)Pd(Y)]$^+$. The resulting charged composition, which will contain protonated octadienyl ligand, is a pi-allyl olefin species. In another embodiment, where 1-methoxy-2,7-octadiene is selected as the methoxyoctadiene compound to start, the complex composition will have the formula [(TMPTA-di-OMe)Pd(Y)]. The resulting neutral composition, which will contain the (non-protonated) octadienyl ligand, is a pi-allyl alkyl complex. The same two ligands (octadienyl and protonated octadienyl) can result where 3-methoxy-1,7-octadiene is selected as the methoxyoctadiene compound to start. Where a methoxyoctadiene compound of either type is selected, but the complex is still in its intermediate form, the resulting composition will include the specific methoxyoctadiene ligand per se, and will be characterized as simply a diene complex. While not wishing to be bound by any theory, it is suggested that the various embodiments of the present invention may include those where one, or two, or all three Y ligands may be present simultaneously in the solution, each as a ligand in its own complex with palladium and the given oxaphosphaadamantane ligand. Each of these embodiments is separately or in any combination thereof useful as a catalyst composition of the present invention, provided, as previously discussed, that the requisite Pd to TMPTA-di-OMe equivalents ratio is applied during the formation thereof.

Successful preparation of the inventive catalyst compositions may be confirmed via analysis of the compositions using any of a variety of standard analytical techniques. Particularly useful and convenient may be well-known techniques such as nuclear magnetic resonance (NM R) spectroscopy, electrospray ionization mass spectrometry (ESI-MS), and combinations thereof. Those skilled in the art will be well aware of methods whereby these instruments may be successfully applied in the identification process.

A particular advantage of the present invention is that the compositions thereof may, in certain particular embodiments wherein the complex is in solution, exhibit surprisingly enhanced solubility and storage stability under most conventional storage conditions. Such conditions may include temperatures ranging from about 0° C. to about 100° C., preferably from about 5° C. to about 60° C., and pressures ranging from about 0 pounds per square inch gauge (psig, approximately 0 kPa) to about 30 psig (approximately 206.8 kPa). The enhanced solubility and storage stability are both unexpected because, as is well-known to those skilled in the art, Pd(II) complexes are reduced slowly, but predictably, under such conditions to form neutral Pd(0) complexes, such as $Pd(PPh_3)_3$ or $Pd(TCMPP)_2(CH_2=C\{(C=O)Me\}_2$. These resulting Pd(0) complexes are typically substantially less soluble in a primary aliphatic alcohol, such as methanol, than are, for example, Pd(II) complexes and, whether used as the initial palladium source or formed as the result of progressive reduction, can precipitate on process equipment surfaces with which they come into contact. Such precipitation may lead to plugging and, therefore, to interruption of processes, such as butadiene telomerization, in which the compositions are used for catalysis purposes. Without wishing to be bound by any theory, it is suggested that the inclusion of the methoxyoctadiene compound in the inventive process, and therefore of any of its ligand forms, as discussed hereinabove, in the inventive compositions, particularly where the process is carried out using the stated preferred ratio of equivalents ranges, imparts a degree of resistance to formation of such insoluble complexes from Pd(II) materials, and/or actually oxidizes Pd(0) materials to convert them back to more soluble Pd(II) materials. The result is, then, improved process operability and reliability when the compositions are to be stored and/or used in, for example, a telomerization reaction.

For purposes hereof, the combination of the palladium metal (which, during the compositions' formation, arises from the palladium source) and the 1,3,5,7-tetramethyl-6-(2,4-dimethoxyphenyl)-2,4,8-trioxa-6-phosphaadamantane ligand in the primary aliphatic alcohol forms a solution. This solution may be generally termed a "catalyst precursor," while addition of the methoxyoctadiene compound thereafter, to form a methoxydiene, octadienyl, or protonated octadienyl ligand in further complex therewith, but without reference to order of addition or of resulting complexation, may be generally understood as serving to convert the "catalyst precursor" to form a "catalyst." Such "catalyst composition" may alternatively be termed a "catalyst solution," since it may be formed via dissolution of its requisite palladium source and sources of the oxaphosphaadamantane ligand and one of the methoxyoctadiene-generated ligands in the primary aliphatic alcohol. It is frequently most convenient to use the catalyst in this form, i.e., as a solution, without further processing. However, it will be understood that the complex can, following its initial formation in solution in the inventive process, be separated from any solvent such that it forms a particulate solid that is typically off-white in color. This particulate solid will, upon analysis (by 1H or 31P nuclear magnetic resonance (NMR) spectroscopy or electrospray-ionization mass spectrometry (ESI-MS)), be shown to exhibit the expected 1:1 stoichiometry of palladium to each ligand. Furthermore, when redissolved in a primary aliphatic alcohol, the resulting catalyst solution will exhibit the invention's improvement in solubility and storage stability, provided that a slight excess of the TMPTA-di-OMe ligand (from greater than 0.1 to 0.3 equivalents, i.e., such that the complex can be re-formed from an equivalents ratio of palladium to TMPTA-di-OMe ranging from greater than 1:1.1 to 1:1.3) is also included in the solution.

The compositions and processes of this invention have particular utility in that they are, and/or result in, a catalyst that requires little, or preferably essentially no, induction time before entering into the reaction wherein butadiene may be telomerized. Such telomerization occurs as a result of formation of a reaction fluid, i.e., from contact between the catalyst composition of the invention and butadiene, typically 1,3-butadiene, and desirably forms a methoxyoctadiene compound. "Reaction fluid" will therefore be understood to include the butadiene, diluents (if any, typically methanol), and the catalyst (which may itself be in solution form in a primary aliphatic alcohol), but may further include, either as part of the catalyst solution or added to the reaction fluid separately, a carboxylic acid and/or promoter.

The telomerization reaction itself is advantageously conducted in a sealed reactor at a pressure at least equal to the sum of vapor pressures of the reaction fluid components, and preferred reaction temperatures preferably range from 25° C. to 120° C. The pressure may be increased above the sum of the vapor pressures by pressurizing an inert gas, such as nitrogen, into the reactor, and is preferably greater than 0.1 megapascal (MPa) (approximately 15 pounds per square inch, psi), and still more preferably greater than 0.4 MPa (approximately 58 psi), to preferably less than 4 MPa (approximately 584 psi), more preferably less than 3 MPa (approxi-mately 438 psi), and still more preferably less than 2 MPa (approximately 292 psi).

The following examples are intended to be illustrative of the present invention and are not intended to be, nor should they be construed as being, limitative of its scope in any way. Comparative examples are also provided to enhance the reader's understanding of certain aspects of the present invention.

EXAMPLE 1

1:1 equivalents ratio, Pd to TMTPA-di-OMe.

In the glovebox, dissolve 94 milliliters (mL) methanol (MeOH), 29 mL 1-methoxy-2,7-octadiene (MOD-1), and 91 microliters (μL) acetic acid (AcOH) to prepare a stock solution that is 25 weight percent (wt %) MOD-1 and 75 wt % methanol.

Dissolve palladium(II) acetylacetonate ($Pd(acac)_2$) (0.0196 grams (g), 0.000064 moles (mol)), 1,3,5,7-tetramethyl-6-(2,4-dimethoxyphenyl)-2,4,8-trioxa-6-phosphaadamantane (TMTPA-di-OMe) (0.0227 g, 0.000064 mol), and 5 mL of the stock solution that is 25 wt % in MOD-1 described above to form an inventive catalyst solution. Allow the catalyst to stir for 3 days at 20° C. before use. Add dibutyl ether ($Bu_2O$, 5 mL) (GC standard), MeOH (13.35 mL), methylcyclohexane (MeCy, 1 mL) (a liquid fill that approximates conditions in a plant reactor), the catalyst (0.15 mL), and a portion of a solution of sodium methoxide (NaOMe) in MeOH (19.32 millimolar (mM), 0.5 mL) to a Fisher-Porter bottle. Seal the bottle with a valve equipped with a septum port. Distill butadiene (approximately 5 mL) into a gas-tight syringe, and determine the mass of butadiene by weighing the syringe before and after addition to the reactor. Inject the butadiene into the Fisher-Porter bottle with the needle placed below the surface of the solution. Place the reaction vessels into preheated oil baths. Remove 1 mL reaction aliquots at the 30 minute (min), 1 hour (h), 2 h, and 4 h time points through a 24 inch (24") needle equipped with a gas-tight valve, and subject each aliquot to gas chromatographic (GC) analysis.

Perform GC analyses on an AGILENT™ 7890A chromatograph (AGILENT is a trademark of Agilent Technologies) using a DB-1701 column at constant gas flow. Use dibutyl ether as the internal standard, and determine response factors based on materials of known composition.
GC Method:
- Column: LTM-DB-1701; Length: 30 meters (m); Diameter: 320 micrometers (μm); Film thickness: 1.0 μL; Mode: constant flow; Initial column flow: 1.27 milliliters per minute (mL/min).
- Front inlet: Mode: split; Initial temp: 250° C.; Pressure: 6.7 pounds per square inch (psi); Split ratio: 50:1.
- Detector: FID; Temp: 260° C.; H$_2$ flow: 40 mL/min; Air flow: 400 mL/min; Make-up gas: He.
- Oven: 250° C.
- Low thermal mass (LTM) column: Initial temp: 50° C. and hold for 2 min; Ramp at 7.5° C./min. Total run time: 22 min.
- Observe no solids precipitation of the catalyst composition after storing for more than 4 weeks.

EXAMPLE 2

After 2 weeks of storage of the catalyst composition of Example 1, conduct a telomerization reaction of butadiene using it, in duplicate, at 70° C. Conversion versus time is shown in Table 1.

TABLE 1

Telomerization reaction run in duplicate at 70° C. Pd:TMTPA-di-OMe = 1:1.

| Time (min) | Conversion of butadiene (%) | Selectivity MOD-1 (%) | Yield MOD-1 (%) |
|---|---|---|---|
| 30 | 49.2/54.8 | 94.3/94.0 | 46.4/51.5 |
| 60 | 68.0/72.5 | 94.6/94.4 | 64.3/68.4 |
| 120 | 84.6/86.0 | 94.8/94.6 | 80.2/81.4 |
| 240 | 91.8/90.0 | 94.8/94.5 | 87.0/85.0 |

EXAMPLE 3

1:1.2 equivalents ratio, Pd to TMTPA-di-OMe.

Prepare the catalyst as in Example 1, but with 0.0273 g (0.000073 mol) TMTPA-di-OMe. Observe that the catalyst shows no solids precipitation after storing for more than 4 weeks.

EXAMPLE 4

After the 4 weeks catalyst storage, use the catalyst composition of Example 3 to conduct a telomerization reaction at 70° C. Conversion versus time is shown in Table 2.

TABLE 2

Telomerization reaction run in duplicate at 70° C. Pd:TMTPA-di-OMe = 1:1.2.

| Time (min) | Conversion of butadiene (%) | Selectivity MOD-1 (%) | Yield MOD-1 (%) |
|---|---|---|---|
| 30 | 62.6/55.6 | 93.5/94.0 | 58.5/52.3 |
| 60 | 72.1/66.0 | 93.7/94.1 | 67.6/62.1 |

TABLE 2-continued

Telomerization reaction run in duplicate at 70° C. Pd:TMTPA-di-OMe = 1:1.2.

| Time (min) | Conversion of butadiene (%) | Selectivity MOD-1 (%) | Yield MOD-1 (%) |
|---|---|---|---|
| 120 | 83.6/79.2 | 93.8/94.2 | 78.4/74.6 |
| 240 | 87.7/83.2 | 93.9/94.2 | 82.4/78.4 |

EXAMPLE 5

1:1.3 equivalents ratio, Pd to TMTPA-di-OMe.

Prepare another catalyst by dissolving Pd(acac)$_2$ (0.3200 g, 0.0011 mol), TMTPA-di-OMe (0.5000 g, 0.0014 mol), 70% acetic acid in water (0.6400 g, 0.0011 mol), MOD-1 (9.1100 g, 0.0650 mol) in MeOH (27.34 g, 34.5 mL). Stir this catalyst for more than 3 days. Dissolve 0.75 g of NaOMe in 300 mL MeOH to make a stock solution of NaOMe promoter. Conduct a telomerization reaction in a Parr reactor at 80° C. with 345 mL of MeOH, 198 g of crude C$_4$ (49.4 wt % butadiene, with the remainder being primarily butanes and butenes), 8.4 mL of the NaOMe stock solution, 15.6 mL of heptane, 12.6 mL of a solution of diethylhydroxamic acid (DEHA) in MeOH (0.021 M), and 2.1 mL of the catalyst. Observe that the catalyst shows no solids precipitation after storing for more than 4 weeks.

EXAMPLE 6

Use the catalyst composition of Example 5 in a butadiene telomerization at 80° C. Conversion of butadiene versus time is shown below in Table 3.

TABLE 3

Telomerization in a Parr reactor at 80° C. Pd:TMTPA-di-OMe = 1:1.3.

| Time (min) | Conversion of butadiene (%) | Selectivity MOD-1 (%) | Yield MOD-1 (%) |
|---|---|---|---|
| 5 | 36.1 | 90.9 | 32.8 |
| 30 | 62.3 | 92.4 | 57.6 |
| 60 | 82.0 | 92.3 | 75.7 |
| 90 | 90.1 | 92.5 | 83.3 |
| 120 | 93.4 | 92.5 | 86.4 |
| 150 | 95.2 | 92.5 | 88.1 |

EXAMPLE 7

1:1.2 equivalents ratio, Pd to TMTPA-di-OMe.

Prepare the catalyst as in Example 1, but with 0.0768 g (0.00020 mol) TMTPA-di-OMe, 0.0510 g Pd(acac)$_2$ (0.00017 mol), 9.1 μL acetic acid (0.00017 mol), 2.148 g 1-methoxy-2,7-octadiene, and 6.315 g methanol. Observe that the catalyst shows no solids precipitation after storing for more than 4 weeks at 40° C.

EXAMPLE 8

Use the catalyst of Example 7 for a telomerization reaction at 60° C. Conversion versus time is shown in Table 4.

TABLE 4

Telomerization reaction run in duplicate at 60° C. Pd:TMTPA-di-OMe = 1:1.2.

| Time (min) | Conversion of butadiene (%) | Selectivity MOD-1 (%) | Yield MOD-1 (%) |
|---|---|---|---|
| 30 | 45.7/37.6 | 96.0/95.7 | 43.9/36.0 |
| 60 | 57.1/58.0 | 95.5/95.6 | 54.5/55.4 |
| 120 | 69.5/74.6 | 95.4/95.4 | 66.3/71.2 |
| 240 | 80.7/84.0 | 95.3/95.3 | 76.9/80.1 |

Comparative Example A

1:1.4 equivalents ratio, Pd to TMTPA-di-OMe.

Prepare the catalyst as in Example 1, but with 0.0307 g (0.000086 mol) TMTPA-di-OMe. After 1 week of catalyst storage, observe the precipitation of a white solid, showing that this equivalents ratio produces an unstable product.

Comparative Example B

1:2 equivalents ratio, Pd to TMTPA-OMe.

Prepare a comparative catalyst using a different but similar oxaphosphaadamantane for the catalyst, i.e., 1,3,5,7-tetramethyl-6-(2-methoxyphenyl)-2,4,8-trioxa-6-phosphaadamantane (TMTPA-OMe), instead of the 1,3,5,7-tetramethyl-6-(2,4-dimethoxyphenyl)-2,4,8-trioxa-6-phosphaadamantane (TMTPA-di-OMe) which is used to form the inventive catalyst. The TMTPA-OMe ligand may be represented schematically as structure (VI):

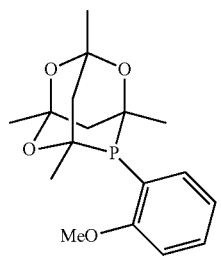

(VI)

To accomplish this, dissolve Pd(acac)₂ (0.7100 g, 0.0024 mol), TMTPA-OMe (1.5000 g, 0.0047 mol), 70% acetic acid in water (0.1410 g, 0.0024 mol), and MOD-1 (19.990 g, 0.1426 mol) in MeOH (60.000 g, 76.00 mL). Stir this catalyst solution for more than 3 days. Observe the precipitation of a white solid.

Comparative Example C

1:1 equivalents ratio, Pd to TMTPA-OMe.

Prepare another comparative catalyst by dissolving Pd(acac)₂ (0.7100 g, 0.0024 mol), TMTPA-OMe (0.7500 g, 0.0024 mol), 70% acetic acid in water (0.1410 g, 0.0024 mol), and MOD-1 (19.990 g, 0.1426 mol) in MeOH (60.000 g, 76.00 mL). Stir this catalyst for more than 3 days. Observe the precipitation of a black solid.

Comparative Example D

1:1.4 equivalents ratio, Pd to TMTPA-OMe.

In a glovebox, dissolve 94 mL methanol (MeOH), 29 mL 1-methoxy-2,7-octadiene (MOD-1), and 91 µL acetic acid (AcOH) to prepare a stock solution that is 25 wt % MOD-1 and 75 wt % methanol.

Dissolve palladium(II) acetylacetonate (Pd(acac)₂) (0.0196 g, 0.000064 mol), 1,3,5,7-tetramethyl-6-(2-methoxyphenyl)-2,4,8-trioxa-6-phosphaadamantane (TMTPA-OMe) (0.0291 g, 0.000090 mol) and 5 mL of the stock solution that is 25 wt % in MOD-1, as described in Comparative Example C, to form a catalyst. Allow the catalyst to stir for 3 days at 20° C. Observe the precipitation of black solids.

Comparative Example E

1:1.8 equivalents ratio, Pd to TMPTA-OMe.

Repeat the pre-catalyst preparation as described in Comparative Example D, but increase the amount of TMPTA-OMe (0.0374 g, 0.000118 mol). Observe the precipitation of white solids.

The above examples and comparative examples illustrate the improved storage stability of the inventive compositions in comparison with compositions comprising a complex having either a different but similar ligand (a 1,3,5,7-tetramethyl-6-(2-methoxyphenyl)-2,4,8-trioxa-6-phosphaadamantane (TMTPA-OMe) ligand instead of a 1,3,5,7-tetramethyl-6-(2,4-di-methoxphenyl)-2,4,8-trioxa-6-phosphaadamantane (TMTPA-di-OMe) ligand, which differ from one another only in the presence or absence of a single methoxy group on the phenyl group), or in comparison with compositions comprising the same ligand but at a Pd to TMTPA-di-OMe equivalents ratio that is outside of the greater than 1:1 to 1:1.3 range that produces a storage-stable and more soluble product. In each of these comparisons, visibly discernible precipitate is encountered in the comparative's performance, either immediately or upon standing for a relatively short period of time, as specified, and therefore telomerization is not attempted therewith. In sharp contrast, telomerizations carried out using the inventive catalyst compositions are very successful.

The invention claimed is:

1. A process to telomerize butadiene comprising contacting butadiene and a catalyst composition comprising a complex comprising palladium, a 1,3,5,7-tetramethyl-6-(2,4-dimethoxyphenyl)-2,4,8-trioxa-6-phosphaadamantane ligand, as set forth in structures (I) and (II),

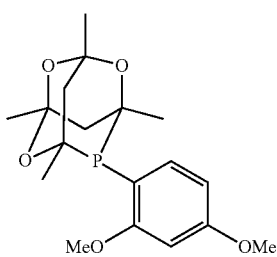

(I)

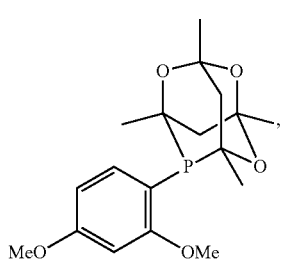

(II)

and a ligand selected from a methoxyoctadiene ligand, an octadienyl ligand, or a protonated octadienyl, under conditions sufficient to telomerize at least a portion of the butadiene.

2. The process of claim 1, wherein the ligand is a methoxyoctadiene ligand.

3. The process of claim 1, wherein the ligand is an octadienyl ligand.

4. The process of claim 1, wherein the ligand is a protonated octadienyl.

\* \* \* \* \*